(12) United States Patent
Hafner et al.

(10) Patent No.: US 12,408,936 B2
(45) Date of Patent: Sep. 9, 2025

(54) SURGICAL INSTRUMENT HAVING A LOCKING MECHANISM

(71) Applicant: Aesculap AG, Tuttlingen (DE)

(72) Inventors: Nikolaus Hafner, Tuttlingen (DE); Justin Danny Cik, Brigachtal (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 18/852,558

(22) PCT Filed: Mar. 28, 2023

(86) PCT No.: PCT/EP2023/058020
§ 371 (c)(1),
(2) Date: Sep. 30, 2024

(87) PCT Pub. No.: WO2023/194160
PCT Pub. Date: Oct. 12, 2023

(65) Prior Publication Data
US 2025/0099124 A1     Mar. 27, 2025

(30) Foreign Application Priority Data

Apr. 4, 2022  (DE) ..................... 10 2022 108 032.3

(51) Int. Cl.
*A61B 17/28* (2006.01)
*A61B 90/00* (2016.01)
*A61B 17/00* (2006.01)

(52) U.S. Cl.
CPC ........ *A61B 17/282* (2013.01); *A61B 17/2833* (2013.01); *A61B 90/08* (2016.02);
(Continued)

(58) Field of Classification Search
CPC ... A61B 17/282; A61B 17/2833; A61B 90/08; A61B 2017/00367; A61B 2017/00876; A61B 2090/0807
See application file for complete search history.

(56) References Cited

U.S. PATENT DOCUMENTS

| | | |
|---|---|---|
| 7,644,848 B2 | 1/2010 | Swayze et al. |
| 9,028,492 B2 | 5/2015 | Kerr et al. |
| (Continued) | | |

FOREIGN PATENT DOCUMENTS

| | | |
|---|---|---|
| CN | 101133972 A | 3/2008 |
| CN | 103687561 A | 3/2014 |
| (Continued) | | |

OTHER PUBLICATIONS

Search Report received in International Application No. PCT/EP2023/058020 dated Jun. 26, 2023, with translation, 6 pages.

(Continued)

*Primary Examiner* — Brooke Labranche
(74) *Attorney, Agent, or Firm* — Christopher A. Rothe; CM Law (57) ABSTRACT

A surgical instrument for clamping and separating tissue has two branches, each forming a clamping jaw and a gripping element. The second branch features a separating element for separating tissue held between the jaws and a drive mechanism for driving the separating element. A locking element is movable between a locking position, in which the locking element engages with the drive mechanism in a blocking manner, and an open position in which the drive mechanism is unblocked by the locking element. The locking element has a magnetic locking portion. The first branch has a magnetic actuating portion for actuating the locking element. The locking portion and/or actuating portion has a magnet to move the locking element into the open position through magnetic attraction or repulsion between the locking portion and actuating portion when the branches approach each other, and to release actuation of the separating element.

16 Claims, 6 Drawing Sheets

(52) U.S. Cl.
CPC ............ *A61B 2017/00367* (2013.01); *A61B 2017/00876* (2013.01); *A61B 2090/0807* (2016.02)

(56) References Cited

U.S. PATENT DOCUMENTS

| | | |
|---|---|---|
| 2006/0089670 A1 | 4/2006 | Hushka |
| 2014/0031821 A1 | 1/2014 | Garrison |
| 2014/0058388 A1 | 2/2014 | Weisshaupt et al. |
| 2015/0136835 A1* | 5/2015 | Shelton, IV ....... A61B 17/3209 227/180.1 |
| 2015/0320483 A1 | 11/2015 | Artale et al. |
| 2018/0325580 A1 | 11/2018 | Sims et al. |

FOREIGN PATENT DOCUMENTS

| | | |
|---|---|---|
| CN | 109077765 A | 12/2018 |
| DE | 102011001372 A1 | 9/2012 |
| DE | 102012110660 A1 | 5/2014 |
| EP | 3235445 A1 | 10/2017 |
| EP | 3400893 B1 | 6/2021 |

OTHER PUBLICATIONS

Search Report received in German Application No. 10 2022 108 032.8 dated Nov. 18, 2022, with translation, 10 pages.
Written Opinion received in International Application No. PCT/EP2023/058020 dated Jul. 10, 2023, with translation, 12 pages.
Office Action received in Chinese Application No. 202380032167.3 dated Mar. 12, 2025, with translation, 11 pages.
Office Action received in Korean Application No. 10-2024-7036671 dated Apr. 2, 2025, with translation, 8 pages.

* cited by examiner

SURGICAL INSTRUMENT HAVING A LOCKING MECHANISM

CROSS-REFERENCE TO RELATED APPLICATIONS

This application is the United States national stage entry of International Application No. PCT/EP2023/058020, filed on Mar. 28, 2023, and claims priority to German Application No. 10 2022 108 032.3. The contents of International Application No. PCT/EP2023/058020 and German Application No. 10 2022 108 032.3 are incorporated by reference herein in their entireties.

FIELD

The present disclosure relates to a surgical instrument for clamping and separating tissue (patient tissue) comprising a first instrument branch and a second instrument branch pivotably hinged to or supported on the first instrument branch, each forming a distal clamping jaw and a proximal grip element, wherein the second instrument branch comprises a tissue separating element for separating patient tissue held between the clamping jaws, and a drive mechanism for driving the tissue separating element, and wherein a locking element is provided for locking or releasing the drive mechanism.

BACKGROUND

Surgical seal and cut instruments are used to grip, seal and separate or cut patient tissue during surgery. They usually have a distal instrument tip on which clamping jaws are provided for gripping and clamping the patient tissue. Moreover, such instruments have a separating or cutting element having a blade or a separating edge, for example, which cuts through the patient tissue. Hand-held instruments also have a handle that the user can hold and on which various actuating elements are provided for actuating a movement of the clamping jaws and/or for actuating the separating or cutting element. In order to prevent the separating or cutting element from being actuated unintentionally, it can usually be locked and unlocked.

From EP 3 400 893 B1, for example, corresponding electrosurgical forceps are known with proximal handles, distal clamping jaws and a blade that can be moved between a retracted and an extended position. A blade lock is provided in one of the handle branches, which prevents distal displacement of the blade and is movable from the locked position to an unlocked position when the jaws are approached to allow distal displacement of the blade. The blade lock has a hook which can be optionally engaged with a blade drive linkage to lock it. A finger connected to the hook protrudes in the direction of the other handle branch. When the handle branches are moved towards each other, the other handle branch presses against the finger, releasing the hook from the blade drive linkage and thus unlocking it.

A problem with the prior art is that an opening must be provided at a point where the finger protrudes from the instrument housing. As a result, particles caused by mechanical friction in the instrument can fall through the opening into the wound or surgical site on the patient and be present there as an unwanted foreign substance/foreign body, putting the patient at risk. This means that there is a high risk of contamination. In addition, liquids (NaCl, blood, etc.) can inadvertently penetrate the instrument and obstruct or damage the mechanics/electronics. To reduce these problems, the spot must be sealed or insulated, which makes the instrument more complex and expensive. In addition, the pin can break off, especially if it is made of plastic. Furthermore, the locking mechanism is relatively complex. Its function can be impaired in particular by aging influences on plastic parts. Furthermore, it is of disadvantage that the blade locking mechanism can be easily bypassed by the user without any tools by manually pressing against the pin or getting caught on it. This increases the risk of injury to the user and the risk of unintentionally cutting through patient tissue. In a case in which a blade actuation is preloaded before the blade is unlocked, the blade may also snap forward abruptly when it is finally unlocked. This can also result in unintentional or uncontrolled cutting and therefore represents a high safety risk.

SUMMARY

The object underlying the present disclosure is to improve or eliminate disadvantages of the prior art. In particular, a surgical instrument for clamping and separating patient tissue is to be provided, which is particularly robust and safe to use.

The task on which the disclosure is based, is solved by a surgical instrument. Advantageous embodiments will be described later in more detail.

More specifically, the problem underlying the disclosure is solved by a surgical instrument for clamping and separating patient tissue, including a first instrument branch and a second instrument branch pivotably hinged to the first instrument branch, which each form a distal clamping jaw and a proximal gripping element. The second instrument branch has a tissue separating element for separating patient tissue held between the clamping jaws and a drive mechanism for driving the tissue separating element. Furthermore, the second instrument branch supports a locking element in such a way that it is movable between a locking position, in which it engages with the drive mechanism in a blocking manner, and an open position, in which the drive mechanism is unblocked by the locking element. The locking element has a magnetic locking portion. The first instrument branch has a magnetic actuating portion in a region opposite the locking element for actuating the locking element. The magnetic locking portion and/or the magnetic actuating portion has/have a magnet in order to move the locking element into the open position by means of magnetic attraction or repulsion between the magnetic locking portion and the first magnetic actuating portion when the instrument branches approach each other and to release actuation of the tissue separating element.

In other words, a generic surgical instrument is provided including a locking element for locking the separating and cutting element, which can be brought into blocking engagement with the drive mechanism. In blocking engagement, i.e. in a locking position, the drive mechanism is blocked and cannot move or can only move slightly. Thus, the tissue separating element cannot be actuated to separate the tissue. If the locking element is not engaged with the drive mechanism, i.e. is in an open position, the drive mechanism and thus the tissue separating element can be actuated optionally by a user. The locking element is at least partially magnetic and can be actuated by a targeted approach or removal of a magnetic actuating portion. The locking element and/or the actuating portion has/have a magnet, in particular a permanent magnet. The locking element is supported in particular so as to be movable transversely to the extension direction of the instrument branches.

A material section or component is to be considered as being magnetic, which is itself a magnet (generates a magnetic field), such as a neodymium magnet, or which can be magnetically attracted by an external magnetic field, but does not necessarily have a magnet itself. This can be, for example, a ferromagnetic metal such as steel or also a permanent magnet. In case of a configuration based on an attractive force, it is advantageous (as described in more detail below) to achieve rapid snapping of the locking element between the locking position and the open position. In case of a suitable layout of the corresponding parameters (e.g. position, shape, size, material of the magnetic elements), in the case of a configuration based on a repulsive force, a low-impact, gradual change of the locking element between the locking position and the open position can be achieved advantageously (as described in more detail below). Alternatively, the layout can also be selected such that a jerky change is achieved.

This has the particular advantage of minimizing the number of openings required in the instrument housing. This also reduces the risk of contamination. All parts of the drive mechanism moreover can be arranged in the instrument housing in a protected manner so that the risk of damage is minimized. In other words, the blade locking mechanism can be completely encapsulated or completely built into the housing. This means that there are no components protruding from the housing and no sealing, insulation etc. is required. Moreover, the instrument can be simpler and more cost-effective. In addition, unintentional unlocking of the drive mechanism is virtually impossible, as a separate magnet is required for this. This minimizes the risk of injury due to unintentional or uncontrolled actuation of the tissue separating element. This means that the blade locking mechanism cannot be manipulated or defeated without tools.

It is particularly advantageous if the locking element is attracted in one direction by the actuating element (or by the reset element). Since a magnetic attractive force is self-reinforcing, it can be achieved thereby that the locking element snaps from the locking position to the open position, i.e. can change to the locking position very quickly. In this way, for example, a half-unlocked position of the locking element can be avoided, so that the risk of a situation can be minimized, in which the tissue separating element abruptly performs a separating movement (e.g. snaps forward) when a switch for actuating the tissue separating element is being actuated and a half-unlocked locking element slips under such a preload. In other words, the locking element cannot change to the released position when the blade actuation is pre-stressed.

The tissue separating element, for example, may have a blade or an edge which is pressed against/moved against the patient tissue held by the clamping jaws and separates it. For tissue separation, the tissue separating element can be mounted in the second instrument branch so as to be movable in the distal direction. Alternatively or additionally, the tissue separating element can be pivotably mounted on one of the clamping jaws. The drive mechanism can connect the tissue separating element to an actuating switch, in particular in a (purely) mechanical manner, which can be actuated by a user. The drive mechanism can, for example, have a linkage and/or a gear drive. The drive mechanism thus has moving components. The present disclosure takes advantage of this and provides the locking element in such a way that it optionally blocks the movement of one or a plurality of the moving components.

The two instrument branches can be hinged to each other in a pivotable manner, in particular at a pivot joint between the clamping jaws and the gripping elements. In particular, portions of the instrument branch distal to the pivot joint are referred to as clamping branch and portions proximal to the joint are referred to as gripping element. The locking element and the magnetic actuating portion are preferably provided on the gripping elements. Alternatively, it is also conceivable to arrange the gripping element and the magnetic actuating portion on the clamping jaws.

Preferably, the second instrument branch has a reset element applying a restoring force to the locking element that counteracts an attractive force or repulsive force between the magnetic locking portion and the magnetic actuating portion in order to exert a restoring force on the locking element acting in the direction of the locking position. Further preferably, the reset element has a spring or a magnetic element.

In other words, a reset element is provided that pre-stresses the locking element into the locking position. This enables the lock to be reliably returned to the locking position when a force exerted on the locking element by the actuating portion decreases. Thus, a position of the lock between the opened and locking position can be set in a controlled manner.

In particular, it is advantageous if the magnetic actuating portion, the magnetic locking portion and the reset element are laid out and positioned relative to one another in such a way that the locking element changes to the open position when a predetermined minimum pressure (a predetermined surface pressure) is applied between the clamping jaws. In other words, the configuration can be such that the blade lock (the locking element) only unlocks, i.e. releases the blade, from a defined pressure in the jaw part (e.g. a minimum pressure of 0.1 N/mm^2 to 0.5 N/mm^2).

The locking element can be a magnet (i.e. a movable slider in which a (locking) magnet is located or which consists of a (locking) magnet) and the reset element and the actuating portion can be magnet-free (i.e. without a magnet of its own). In this case, only one magnet is required, which is particularly cost-effective. The locking element can optionally form a protective cover around the magnet or magnetic portion possibly accommodated therein (overmolded/completely encapsulated by it) or be coupled to it in a material-fit, force-fit or form-fit manner. Alternatively, the locking element can be magnet-free and the actuating portion and possibly the reset element can have one or more magnets. This is advantageous because the locking element moves back and forth between two positions and can stop in the respective end positions, which could damage a permanent magnet, which typically has brittle materials.

Advantageously the magnetic actuating portion, the magnetic locking portion and the reset element are designed and positioned relative to one another such that the locking element is held in the locked position in a defined first position of the instrument branches relative to each other, and is held in a defined second position of the instrument branches relative to each other in the open position. In particular, the distal clamping jaws are opened in the first position and are in a predetermined clamping position in the second position.

In other words, the reset element, particularly if this is a magnetic element, and/or the actuating portion can be formed at a fixed position in the respective instrument branch. The advantage of this is that it is easy to set exactly when the locking element moves between the open position and the locking position. In other words, a functional balance can be achieved by adjusting the individual distances and/or positions and/or dimensions of the magnetic portions or elements (i.e. the locking element and/or the actuating portion and/or the reset element) and/or a strength of the magnet(s) used therein relative to each other. This can be achieved, for example, by the locking element changing to the open position precisely when a defined surface pressure is applied between the clamping jaws or immediately before the clamping jaws touch each other or precisely when they come into contact with each other, or at any other time. When designing and positioning the locking element, the actuating portion and, if applicable, the reset element, it is preferable to take into account which other magnetic (e.g. metallic or magnetic) bodies or surfaces are installed in the instrument.

In this way, actuation of the locking element can be directly coupled to the fact when the clamping jaws are in a position suitable for separating the tissue. Furthermore, separation of the tissue outside this position can be avoided.

The instrument according to the present disclosure further has the advantage that a change of the locking element into the open position and/or into the locking position takes place suddenly. This allows the locking element to stop at corresponding end positions. As described in more detail below, the stop can either be damped or used to provide feedback to a user about the shift of the locking element.

According to an advantageous embodiment, a movement of the locking element is limited by a damper stop. In this case, a damper portion can be provided on the damper stop and/or on the locking element on a side facing the damper stop in order to dampen an impact of the locking element on the damper stop.

In other words, a movement of the locking element is damped at least in one direction or its end stop. This is particularly advantageous if the end stop and/or the locking element have a brittle material that could be damaged by the locking element hitting it. The damper portion, for example, may have an elastomer and/or a spring and/or a damper fluid. For example, an intermediate space between the locking element 15 and its guide in the area of its end stops/end positions can be airtight or can throttle outflowing air so that the air in this intermediate space can respectively serve as a damper portion. In addition to the magnetic locking portion, the locking element hence may have a (possibly damping) slider portion coupled to it.

Alternatively or additionally, according to a further advantageous embodiment, a movement of the locking element can be limited by a signal transmitter stop. On the signal transmitter stop and/or on the locking element on a side facing the signal transmitter stop, a signal transmitter portion can be provided in this case, which generates or amplifies a tactile and/or audible feedback when the locking element hits the signal transmitter stop in order to signal to the user that the locking position and/or the open position has been reached.

In other words, a (tactile) feedback or a sound (a click) can be generated when the slider moves/the positions of the locking element change. A signal transmitter stop is a stop of the locking element at one of its end positions, in which an audible or tactile signal is generated when it stops, e.g. when two hard surfaces meet. For example, the signal transmitter stop portion may have a brittle and/or bright or loud sounding and/or vibrating material. This allows a feedback or signal to be generated or amplified when the locking element hits the signal transmitter stop. The feedback/signal advantageously indicates to the user that he has reached a specific position of the clamping jaws in relation to each other, e.g. that there is a predetermined surface compression between the clamping jaws, which is required for tissue separation and possibly tissue coagulation. In addition, the user immediately recognizes thereby that he/she may now actuate the tissue separating element. The signal thus can be used as a safety feature.

The surgical instrument may also have an instrument housing, which preferably has a window in the area of the locking element. A region of the locking element located behind the window may form a visible marker portion that identifies the locking state and/or the opened state.

In other words, preferably a portion of the locking element that is located behind the window in the opened state (i.e. is thus visible on the outside of the instrument) has a first marking (e.g. being red) and a further portion of the locking element that is located behind the window in the locking state has a second marking (e.g. green). The markings can be, for example, equal to the marking of poles of the magnet (i.e. a magnetic locking portion) of the locking element. This has the advantage for the user that the position of the locking element is immediately apparent to him/her at all times (also independently of a feedback of the signal transmitter stop). This means that the respective state of the blade lock can be visually communicated to the user. The marker portion can only have the first and second markings or can indicate a gradual or smooth transition between the first and second markings or between the open position and the locking position.

Moreover, it is also conceivable that the window (the optical viewing window) could be used to indicate if the user is pressing too hard, i.e. if the pressure/surface compression in the jaw/between the clamping jaws is larger than e.g. 2 N/mm2. For example, a specific position of the locking element (e.g. a displacement beyond the open position) or a display/state of another indicator component arranged behind the window in the housing, which shows the pressure/exceeding of a limit pressure, may serve as an indicator for excessive pressure between the clamping jaws.

It is also preferred when the drive mechanism has an actuating switch that can be operated by a user to actuate the tissue separating element. In addition, the drive mechanism can have a pre-stressing element that pre-stresses the tissue separating element into an unactuated position. This allows the user to actuate/trigger the tissue separating element in one direction only (to separate the tissue) and the tissue separating element then automatically returns to its initial position. This makes the instrument particularly easy to use.

Advantageously, the drive mechanism has a drive or toothed rack and the locking element is mounted so that it can move transversely to the toothed rack such that it engages in a movement path of the toothed rack in the locking position and is located outside the movement path of the toothed rack in the open position. This is particularly advantageous as it represents a very simple, space-saving and cost-effective structure. The locking element can engage particularly easily in the movement path of the toothed rack. For example, a (driving) input toothed rack can be coupled to the actuating switch and a (driven) output rack can be coupled to the tissue separating element and a gearwheel can couple these racks. As an alternative to the toothed rack path, the locking element may also engage in the gearwheel if necessary.

Preferably, the toothed rack and the locking element are formed and arranged relative to each other such that the locking element in the locking position engages in teeth of the toothed rack or in an undercut opposite the teeth. Further preferably, the locking element engages around the toothed rack in a U-shape or O-shape, at least in the locking position. In the latter case, the locking element can also be wedgeshaped. Furthermore, the locking element can be arranged particularly flexibly, i.e. along the entire toothed rack in the instrument. Accordingly, the overall structure is particularly simple. Moreover, in the case of the at least partially U-shaped or O-shaped locking element, it is advantageous that the design based on a (magnetic or resilient) repulsive force between the locking element and the reset element and the actuating portion, respectively, is easy to implement. Alternatively, the locking element may engage behind one end of one of the toothed racks.

Furthermore, it is advantageous if the reset element is a magnetic portion of the drive mechanism, such as a guide rail or plate in which one of the toothed racks is guided. This allows the corresponding portion to fulfill a double function and eliminates the need for a separate component as a reset element. This further simplifies the structure and makes it more cost-effective.

In other words, the problem underlying the invention can be solved, for example, as follows.

A surgical instrument has a first and second shaft (instrument branches), which are pivotably connected to each other, and a cutting blade as an example of a tissue separating element. To activate the cutting blade, a user places a finger on a cutter trigger (i.e. an actuation switch), e.g. in the form of a slider. As soon as he/she pulls the cutter trigger towards him/her, it drives a toothed rack, which drives a driven toothed rack via a gear wheel. The driven toothed rack pushes the blade along with it. This mechanism is reset via a spring as an example of a pre-stressing element, which acts on the driven toothed rack, for example, to pull it back into its initial position. A blade lock is used to lock this mechanism magnetically. For example, permanent neodymium magnets with different or equal holding force are used.

When the instrument is in an opened state, the slider/locking element is pulled towards the reset element by the magnet (in the locking element or the reset element). In this position, the slider blocks the movement of a driving/input toothed rack so that the tissue separating element cannot be actuated. As the two instrument branches approach each other, the locking element is increasingly attracted towards the magnetic actuating portion (which may have a magnet). This causes the locking element to move in the direction of the actuating portion. When the locking element finally hits a corresponding stop in the housing, a path for the drive mechanism/the blade mechanism/a drive train for driving the tissue separating element is free. The tissue separating element can therefore be actuated.

When the instrument opens or the instrument branches move away from each other, the attraction between the locking element and the actuating element becomes so weak from a certain point that the attractive force to the reset element becomes stronger. The locking portion then moves back in the direction of the reset element and thus into the locking position.

BRIEF DESCRIPTION OF THE DRAWINGS

In the following, the present disclosure is described by means of preferred embodiments. However, these are only illustrative in nature and are not intended to restrict the scope of protection of the present invention. Furthermore, in the description of the various embodiments, equal reference signs are used for equal components in order to avoid redundant descriptions thereof.

DETAILED DESCRIPTION

Figure 1:
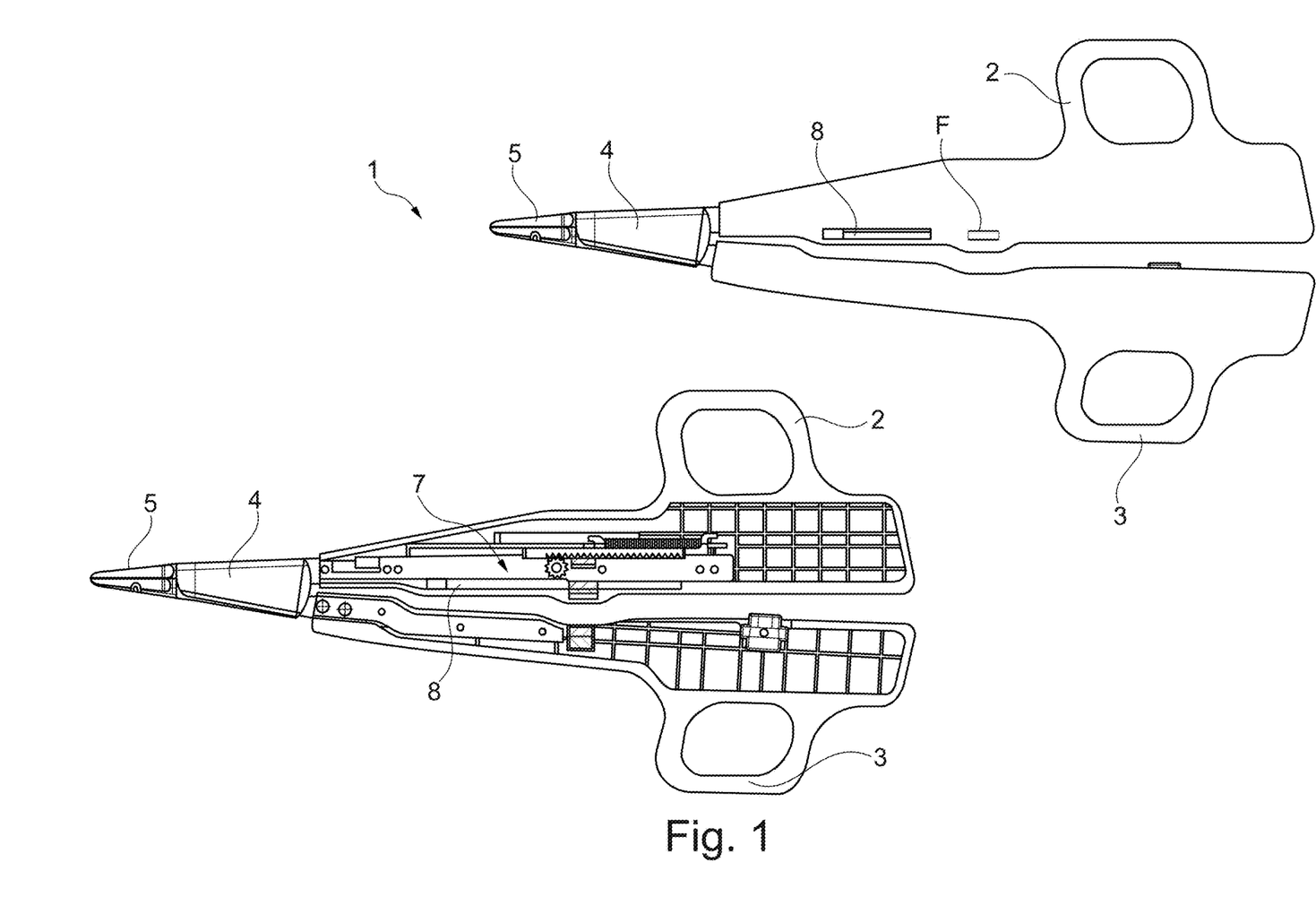
FIG. 1 shows an instrument according to a first preferred embodiment of the present disclosure from the outside and with the instrument housing disassembled.

FIG. 1 shows an instrument 1 according to a first preferred embodiment of the present disclosure from the outside (top) and with the instrument housing disassembled (bottom). The instrument 1 has a first instrument branch 2 and a second instrument branch 3, which are hinged to each other at a hinge portion/pivot joint 4. Distally from the pivot joint 4, the instrument branches 2, 3 form clamping jaws 4 and proximally thereof handle portions. A drive mechanism 7 is arranged in the handle portion of the second instrument branch, which can be actuated by a user via an actuating switch 8 and can be locked and unlocked, as is described in more detail below. Moreover, the housing can have a window F, behind which a locking element 15, described in more detail below, is located, the surface of which can form a marker portion in the area of the window F to indicate a state/position of the locking element 15.

Figure 2:
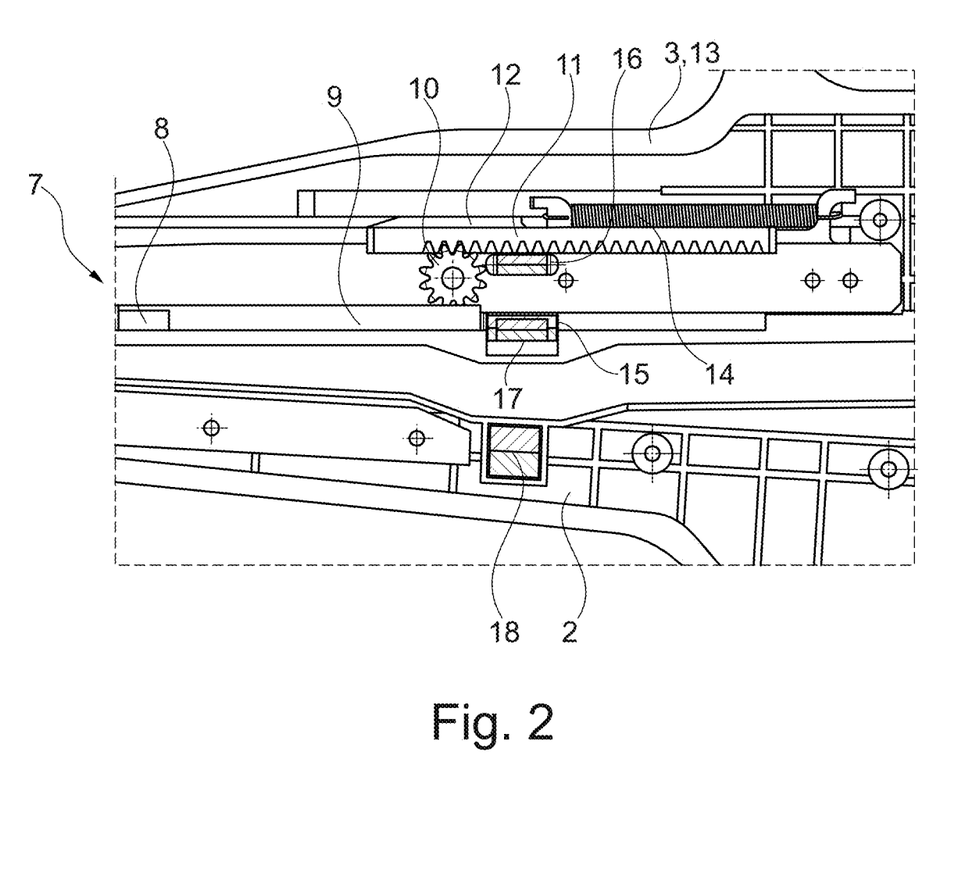
FIG. 2 shows a detailed view of a drive mechanism of the instrument of the first embodiment.

FIG. 2 shows a detailed view of a drive mechanism 7 of the instrument 1 of the first embodiment. The two instrument branches 2, 3 are open, i.e. swiveled away from each other around pivot joint 4. The actuating switch 8 is connected to a drive/input toothed rack 9. The input toothed rack 9 drives a gear wheel 10, which again drives an output rack 11. The output rack 11 is directly or indirectly connected to a tissue separating element 12 (in this case an advancing blade slider). In the present embodiment, the tissue separating element 12 is unactuated and locked, i.e. arranged in a proximal position. The output rack 11 or the tissue separating element 12 is connected to an instrument housing 13 of the second instrument branch 3 via a pre-stressing element 14 in the form of a spiral tension spring, which pre-stresses the tissue separating element 12 into an unactuated starting position.

Figure 3:
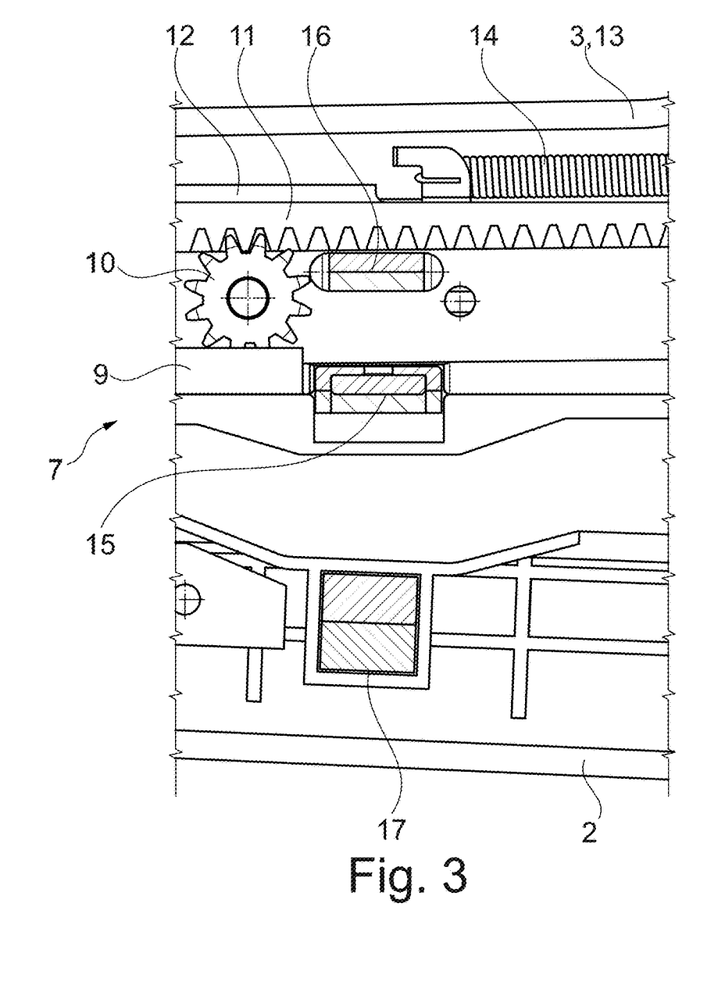
FIG. 3 and FIG. 4 show a locking mechanism of the first embodiment in a locking position and an open position.

In the present illustration and enlarged in FIG. 3, the drive mechanism is blocked by a locking mechanism with a locking element 15, i.e. the locking element 15 is in a locking position. The locking element 15 has a magnet which is aligned such that its one pole faces the first instrument branch and the other pole faces away from it. On its other pole, the locking element 15 has a cap that partially encloses the magnet and engages behind a proximal end of the drive rack. The cap can serve as a damper portion for damping a stop of locking element 15 in the locking position. Alternatively, the cap can serve as a signal transmitter portion which, for example, serves to emit a particularly loud noise when the locking element 15 stops in its corresponding end position (i.e. at the signal transmitter stop). On a side opposite the other pole, a further magnet is attached in the instrument housing 13 of the second instrument half 3 as a reset element 16. The magnet of reset element 16 has a pole oriented attractively in the direction of the magnet of locking element 15. The locking element 15 is held in the locking position by an attraction between the magnet of locking element 15 and reset element 16. In an area in the handle portion of the first instrument branch 2 opposite the locking element 15, a magnetic actuating element 17 is attached, which also has a further magnet, one pole of which is aligned towards the locking element 15.

Figure 4:
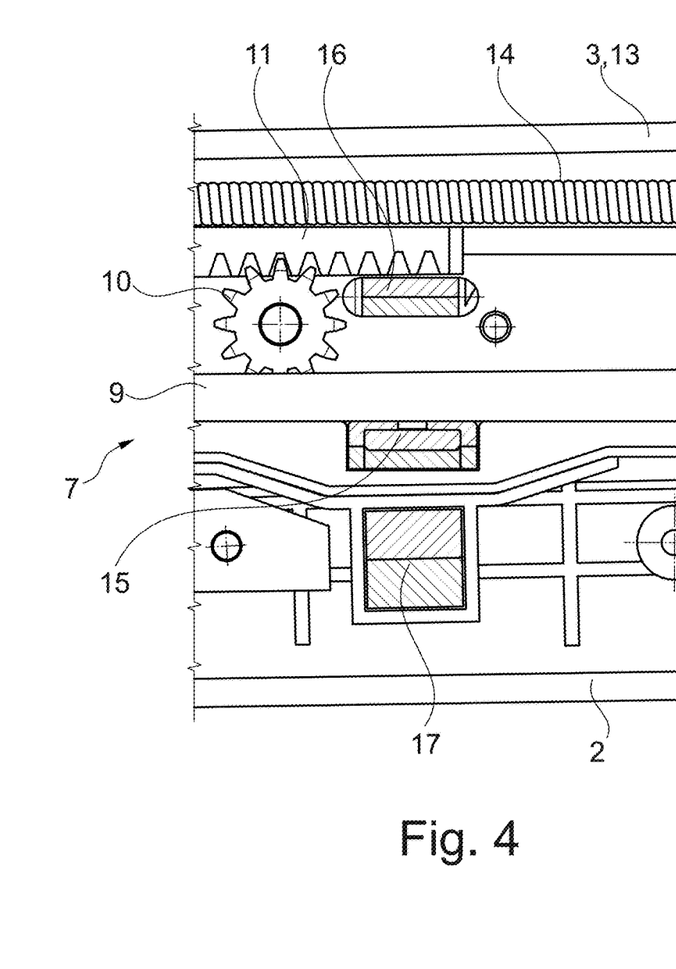

In FIG. 4, the two instrument branches 2 and 3 are closed. The actuating element 17 is closer to the magnet of locking element 15 than in the position in instrument 1 as shown in FIGS. 2 and 3. As a result, there is an attractive force between the actuating element 17 and reset element 16 and locking element 15. As a result, locking element 15 is shifted towards actuating element 17 and no longer engages proximally behind the drive rack 9, i.e. the locking element 15 is in an open position. Thus, the drive rack 9, as shown here, can be shifted in the proximal direction and actuate the tissue separating element 12.

Further embodiments are described below, which preferably correspond to the first embodiment except for the differences explained subsequently.

Figure 5:
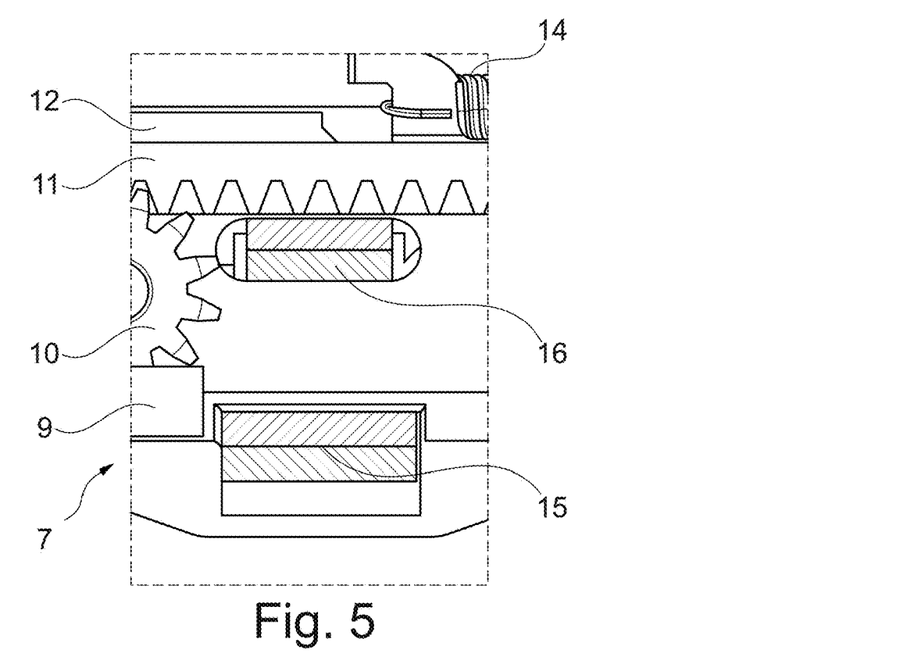
FIG. 5 and FIG. 6 illustrate, respectively, a modification of the locking mechanism according to a second and a third embodiment of the present disclosure.
Figure 6:
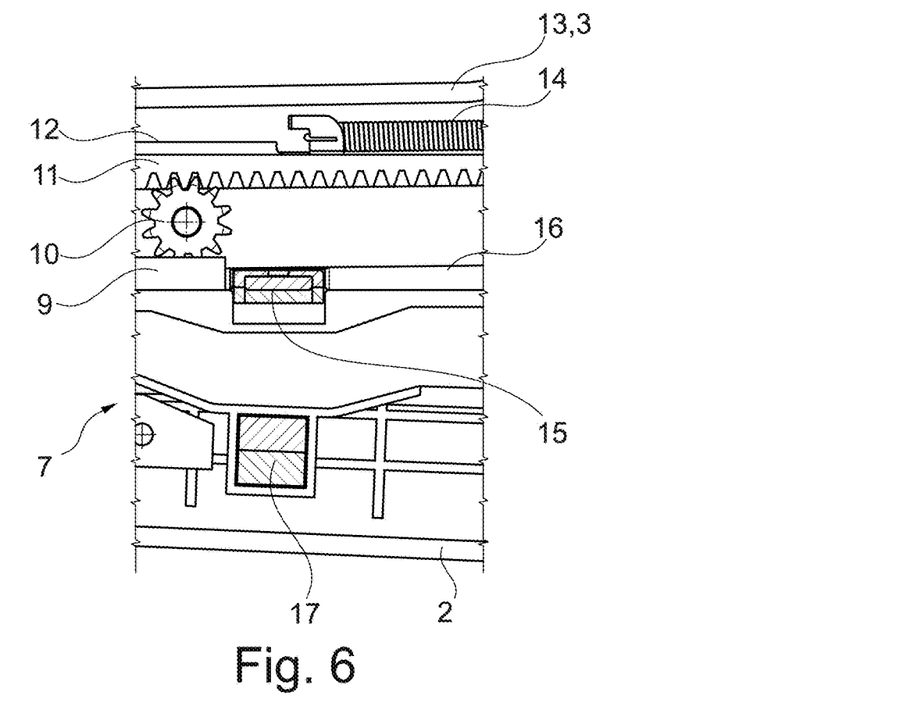

FIG. 5 illustrates a modification of the locking mechanism according to a second embodiment of the present disclosure. According to this modification, the locking element 15 has no cap. FIG. 6 illustrates a further modification of the locking mechanism according to a third embodiment of the present disclosure. In this embodiment reset element 16 is formed by a metallic guide rail of drive rack 9. The reset element 16 thus does not have a magnet.

Figure 7:
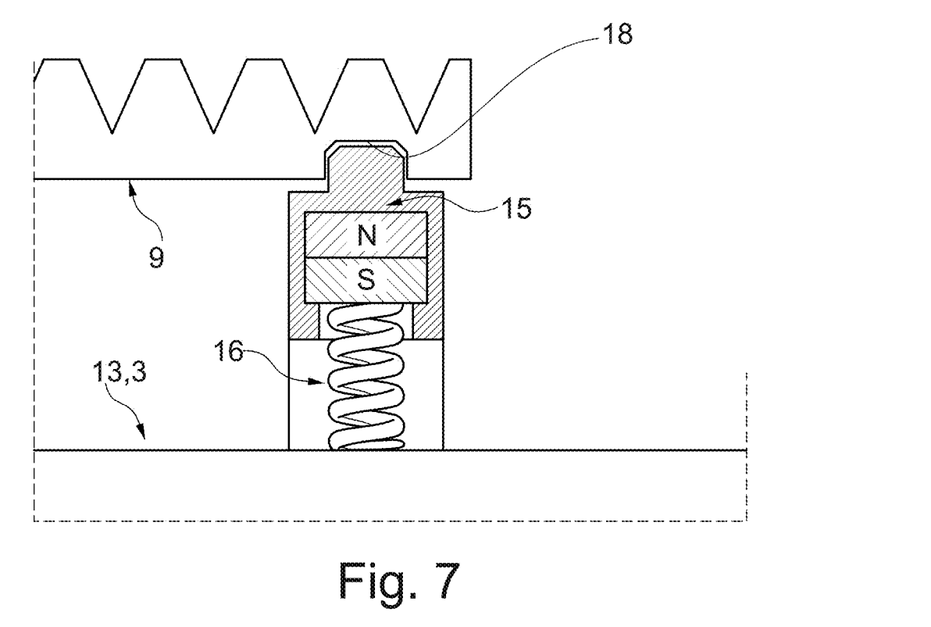
FIG. 7 and FIG. 8 illustrate a modified locking mechanism according to a fourth preferred embodiment in a locking position and an open position.
Figure 8:
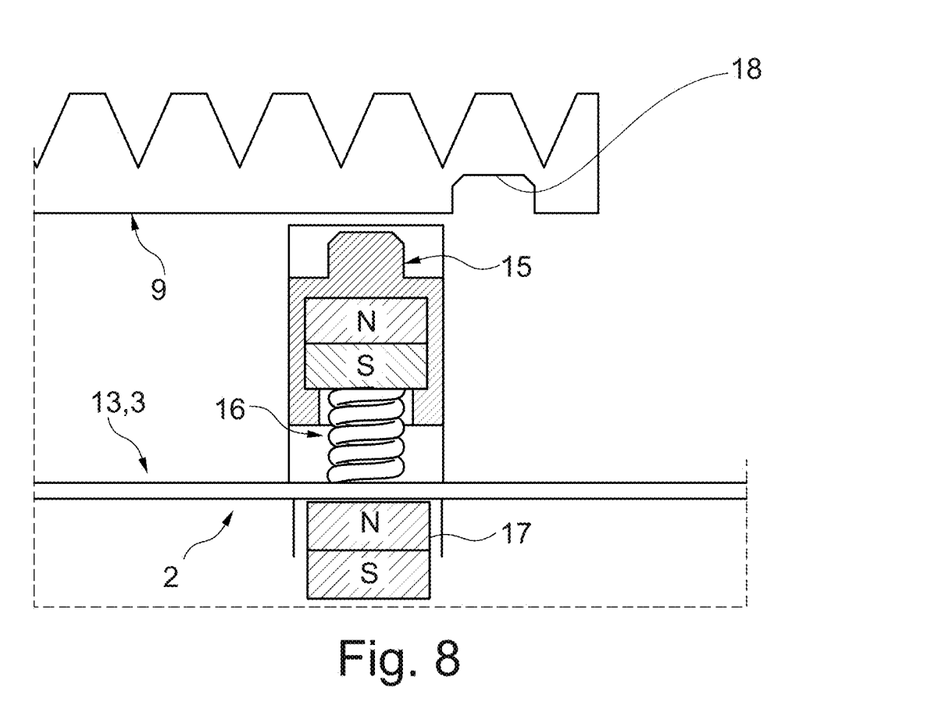

FIG. 7 and FIG. 8 show a modified locking mechanism according to a fourth preferred embodiment in a locking position and in an open position, respectively. The drive rack 9 has a toothed side and a toothless side. An undercut 18 is formed on the toothless side, which is designed to engage with the locking element 15 or a cap thereof. The reset element 16 is formed as a (spiral) spring. This spring supports itself between the locking element 15 and the instrument housing 13 of the second instrument branch 3. When the first instrument half 2 approaches, as shown in FIG. 8, a magnetic force of attraction between the locking element 15 and the actuating portion 17 overcomes a spring force of the reset element 16, so that the locking element 15 is pulled back into the open position.

Figure 9:
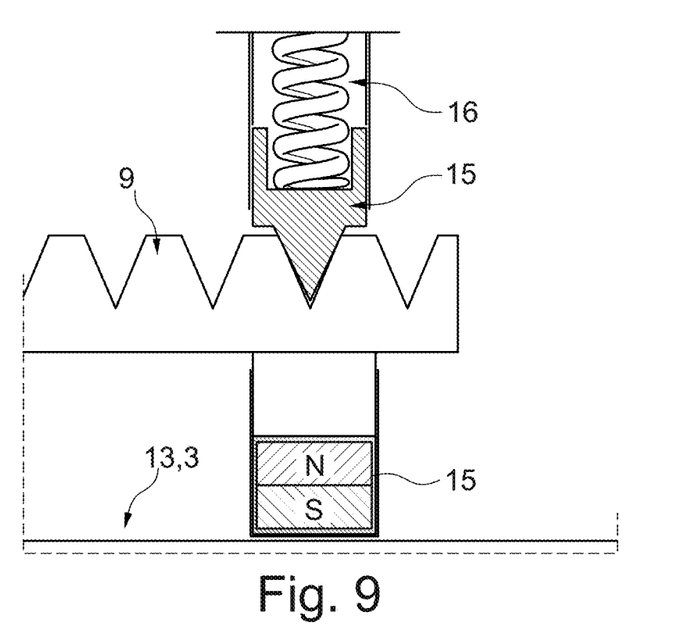
FIG. 9 and FIG. 10 show a modified locking mechanism according to a fifth preferred embodiment in a locking position and an open position.
Figure 10:
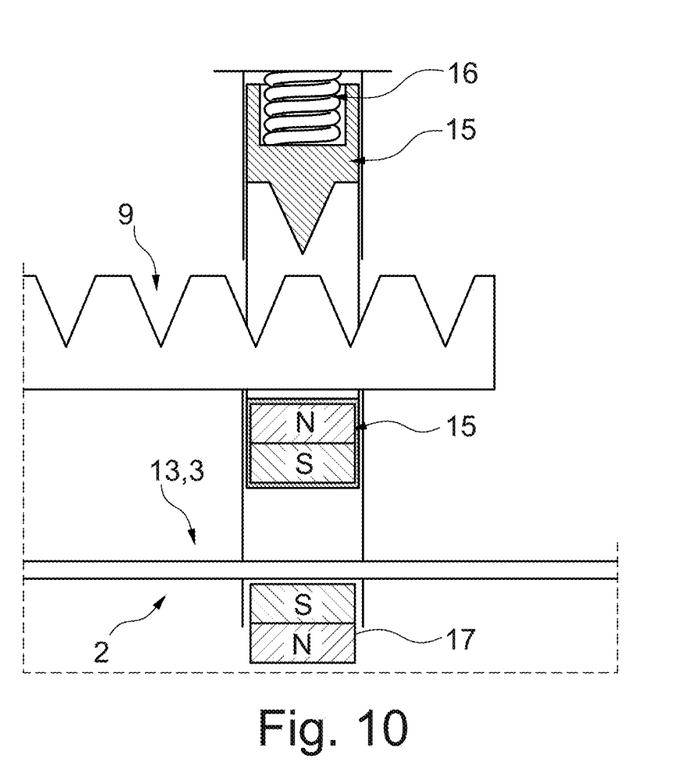

FIG. 9 and FIG. 10 show a modified locking mechanism according to a fifth preferred embodiment in a locking position and an open position, respectively. The locking element 15 is designed as a U-shaped or O-shaped gripper, which grips around the drive rack 9. On a gripper side facing the first instrument branch 2, the locking element 15 has a magnet. On its gripper side opposite the first instrument branch 2, the locking element has an engagement portion, which is formed to engage with the teeth of the drive rack 9. The reset element 16 is designed as a (spiral) spring, which presses against the locking element 15 on the gripper side opposite the first instrument branch 2 in order to pre-stress it into the locking position, as shown in FIG. 9. When the first instrument half 2 approaches, as shown in FIG. 10, a magnetic repulsion force between the locking element 15 and the actuating portion 17 overcomes a spring force of the reset element 16, so that the locking element 15 is pulled back/pushed back into the open position.

LIST OF REFERENCE SIGNS

1 Instrument
2 First instrument branch
3 Second instrument branch
4 Pivot joint/joint section
5 Clamping jaws/distal instrument tip
7 Drive mechanism
8 Actuating switch
9 Drive/input rack
10 Gear wheel
11 Driven/output rack
12 Tissue separating element/blade slider
13 Housing of the second instrument branch
14 Pre-stressing element/tension spring
15 Magnetic locking element
16 Magnetic reset element
17 Magnetic actuating element
18 Undercut
F Window/viewing window

The invention claimed is:

1. A surgical instrument for clamping and separating patient tissue, having a first instrument branch and a second instrument branch which is pivotably articulated on the first instrument branch and which each form a distal clamping jaw and a proximal gripping element, wherein
the second instrument branch comprises a tissue separating element for separating patient tissue held between the clamping jaws and a drive mechanism for driving the tissue separating element and supports a locking element such that it is movable between a locking position, in which it engages the drive mechanism in a blocking manner, and an opened position, in which the drive mechanism is unblocked by the locking element, wherein
the locking element has a magnetic locking portion and the first instrument branch has a magnetic actuating portion for actuating the locking element at a region opposite the locking element, the magnetic locking portion and/or the magnetic actuating portion having a magnet, in order to move the locking element into the opened position by a magnetic attraction or repulsion between the magnetic locking portion and the first magnetic actuating portion when the instrument branches approach each other and to release actuation of the tissue separating element.

2. The surgical instrument according to claim 1, wherein the second instrument branch comprises a reset element which applies a restoring force to the locking element which counteracts an attractive force or repulsive force between the magnetic locking portion and the magnetic actuating portion to exert a restoring force on the locking element acting in a direction of the locking position.

3. The surgical instrument according to claim 2, wherein the magnetic actuating portion, the magnetic locking portion and the reset element are configured and positioned relative to each other in such a way that the locking element is held in the locking position in a first position of the instrument branches relative to each other and is held in the opened position in a second position of the instrument branches relative to each other.

4. The surgical instrument according to claim 3, wherein the distal clamping jaws are open in the first position and are in a predetermined clamping position in the second position.

5. The surgical instrument according to claim 3, wherein the magnetic actuating portion, the magnetic locking portion and the reset element are configured and positioned relative to each other such that the locking element changes to the opened position when a predetermined pressure is applied between the clamping jaws.

6. The surgical instrument according to claim 2, wherein the reset element comprises a spring or a magnetic element.

7. The surgical instrument according to claim 1, wherein a movement of the locking element is limited by a damper stop and a damper portion is provided on the damper stop and/or on the locking element on a side facing the damper stop in order to dampen an impact of the locking element on the damper stop.

8. The surgical instrument according to claim 1, wherein a movement of the locking element is limited by a signal transmitter stop and the signal transmitter stop and/or the locking element is provided with a signal transmitter portion on a side facing the signal transmitter stop, which generates or amplifies a tactile and/or audible feedback when the locking element hits the signal transmitter stop, in order to signal to a user that the locking position and/or the opened position has been reached.

9. The surgical instrument according to claim 1, further comprising an instrument housing which has a window in the region of the locking element, wherein a region of the locking element lying behind the window forms a marker portion which characterizes the locking position and/or the opened position.

10. The surgical instrument according to claim 1, wherein the drive mechanism comprises an actuating switch actuatable by a user for actuating the tissue separating element and a pre-stressing element which pre-stresses the tissue separating element into an unactuated position.

11. The surgical instrument according to claim 1, wherein the drive mechanism comprises a toothed rack and the locking element is movable transversely to the toothed rack such that in the locking position it engages in a movement path of the toothed rack and in the opened position it is located outside the movement path of the toothed rack.

12. The surgical instrument according to claim 11, wherein the toothed rack and the locking element are configured and arranged in such a way that the locking element engages in the locking position in teeth of the toothed rack or in an undercut opposite the teeth.

13. The surgical instrument according to claim 11, wherein the locking element engages around the toothed rack in a U-shape at least in the locking position.

14. A surgical instrument for clamping and separating patient tissue, having a first instrument branch and a second instrument branch which is pivotably articulated on the first instrument branch and which each form a distal clamping jaw and a proximal gripping element, wherein
the second instrument branch comprises a tissue separating element for separating patient tissue held between the clamping jaws and a drive mechanism for driving the tissue separating element and supports a locking element such that it is movable between a locking position, in which it engages the drive mechanism in a blocking manner, and an opened position, in which the drive mechanism is unblocked by the locking element, wherein
the locking element has a magnetic locking portion and the first instrument branch has a magnetic actuating portion for actuating the locking element at a region opposite the locking element, the magnetic locking portion and/or the magnetic actuating portion having a magnet, in order to move the locking element into the opened position by a magnetic attraction or repulsion between the magnetic locking portion and the first magnetic actuating portion when the instrument branches approach each other and to release actuation of the tissue separating element;
wherein the drive mechanism comprises a toothed rack and the locking element is movable transversely to the toothed rack such that in the locking position it engages in a movement path of the toothed rack and in the opened position it is located outside the movement path of the toothed rack.

15. The surgical instrument according to claim 14, wherein the toothed rack and the locking element are configured and arranged in such a way that the locking element engages in the locking position in teeth of the toothed rack or in an undercut opposite the teeth.

16. The surgical instrument according to claim 14, wherein the locking element engages around the toothed rack in a U-shape at least in the locking position.

* * * * *